United States Patent
Brown et al.

(10) Patent No.: US 11,087,886 B1
(45) Date of Patent: Aug. 10, 2021

(54) COMPUTING SYSTEM FOR NOTIFYING PERSONS OF EXPOSURE TO AN INFECTIOUS DISEASE IN A HEALTHCARE FACILITY

(71) Applicant: Allscripts Software, LLC, Raleigh, NC (US)

(72) Inventors: Joshua Brown, Cary, NC (US); Dave Windell, Raleigh, NC (US)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 299 days.

(21) Appl. No.: 16/192,843

(22) Filed: Nov. 16, 2018

(51) Int. Cl.
*G16H 50/80* (2018.01)
*G16H 10/60* (2018.01)

(52) U.S. Cl.
CPC ............ *G16H 50/80* (2018.01); *G16H 10/60* (2018.01)

(58) Field of Classification Search
CPC .... G06F 1/00–2221/2153; G16H 10/00–80/00
See application file for complete search history.

(56) References Cited

U.S. PATENT DOCUMENTS

| | | | |
|---|---|---|---|
| 7,496,960 B1 * | 2/2009 | Chen | G06F 21/56 726/22 |
| 7,873,344 B2 | 1/2011 | Bowser et al. | |
| 9,729,833 B1 * | 8/2017 | Kusens | G16H 40/20 |
| 2003/0204130 A1 | 10/2003 | Colston, Jr. et al. | |
| 2007/0219645 A1 * | 9/2007 | Thomas | G05B 15/02 700/29 |
| 2009/0065596 A1 * | 3/2009 | Seem | F24F 11/30 236/51 |
| 2009/0265106 A1 * | 10/2009 | Bearman | G06Q 10/00 701/300 |
| 2013/0318027 A1 * | 11/2013 | Almogy | G16H 50/80 706/52 |

(Continued)

FOREIGN PATENT DOCUMENTS

| | | | |
|---|---|---|---|
| JP | 2016218598 A | * | 5/2015 |
| KR | 20180098053 A | | 9/2018 |

OTHER PUBLICATIONS

Toda et al., "Effectiveness of a Mobile Short-Message-Service-Based Disease Outbreak Alert System in Kenya," Emerging Infectious Diseases, vol. 22, No. 4 (Year: 2016).*

*Primary Examiner* — Elaine Gort
*Assistant Examiner* — Jonathon A. Szumny
(74) *Attorney, Agent, or Firm* — Medley, Behrens & Lewis, LLC

(57) ABSTRACT

An electronic health records application (EHR) receives an indication that a patient in a healthcare facility has been diagnosed with an infectious disease at a datetime. The EHR determines first locations in the healthcare facility in which the patient has been present. The EHR identifies portions of a heating, ventilation, and air conditioning system (HVAC) system of the healthcare facility based upon the first locations. The portions of the HVAC system connect the first locations to second locations in the healthcare facility. The EHR identifies a person that has been present in at least one of the first locations or the second locations. The EHR then causes a notification to be transmitted to a computing device operated by the person notifying the person of potential exposure to the infectious disease.

19 Claims, 8 Drawing Sheets

(56) References Cited

U.S. PATENT DOCUMENTS

| | | | |
|---|---|---|---|
| 2014/0368335 A1* | 12/2014 | Jordan | G08B 25/016 |
| | | | 340/539.13 |
| 2016/0132652 A1 | 5/2016 | Chapman Bates et al. | |
| 2016/0314256 A1* | 10/2016 | Su | G06N 20/00 |
| 2016/0342770 A1 | 11/2016 | Unser et al. | |
| 2017/0169182 A1* | 6/2017 | Silva | G16H 50/70 |
| 2017/0352119 A1* | 12/2017 | Pittman | G06F 16/29 |
| 2018/0049652 A1* | 2/2018 | Al Ahmad | G16H 50/20 |
| 2018/0181714 A1* | 6/2018 | Pillarisetty | G16H 50/30 |
| 2018/0324393 A1* | 11/2018 | Ryan | G06K 9/2018 |
| 2019/0122759 A1* | 4/2019 | Wakimoto | G16H 50/30 |
| 2019/0259472 A1* | 8/2019 | Goodreau | G16B 5/00 |
| 2019/0380661 A1* | 12/2019 | Al Ahmad | A61B 5/7246 |
| 2020/0013102 A1* | 1/2020 | Yeldham | G06Q 30/0625 |
| 2020/0168333 A1* | 5/2020 | Kalakuntla | G06F 16/00 |
| 2020/0176125 A1* | 6/2020 | Chatterjea | G16H 40/20 |
| 2020/0178906 A1* | 6/2020 | Bevan | A61B 5/1032 |
| 2020/0302452 A1* | 9/2020 | Platt | G06Q 30/02 |

* cited by examiner

COMPUTING SYSTEM FOR NOTIFYING PERSONS OF EXPOSURE TO AN INFECTIOUS DISEASE IN A HEALTHCARE FACILITY

BACKGROUND

Electronic health records applications (EHRs) are computer-executable applications that are configured to assist healthcare workers with providing care to patients. EHRs are configured with functionality pertaining to patient intake, patient billing, insurance billing, prescription generation, maintaining a record of patient care over time, etc. EHRs are often used by healthcare workers at the point of care (i.e., at a time when the healthcare worker is providing care to a patient). For example, a healthcare worker may retrieve data from a patient record maintained by an EHR to relatively quickly ascertain problems being experienced by the patient, medications currently being taken by the patient, and so forth.

When a patient in a healthcare facility is diagnosed with an infectious (i.e., contagious) disease, healthcare workers in the healthcare facility typically follow certain standardized procedures in order to prevent the infectious disease from spreading to other persons in the healthcare facility. For instance, the patient may be placed in isolation in a negative pressure room in order to prevent spread of the infectious disease. Additionally, notifications may be sent to anyone in the healthcare facility who may have been exposed to the infectious disease by being in proximity to the patient. Conventionally, an EHR receives manual input from a healthcare worker in order to ascertain identities of persons who may have been exposed to the infectious disease. For instance, the EHR may receive an identifier for the patient as input from a healthcare worker, and the EHR may determine identities of healthcare workers and patients that were in proximity to the patient in the healthcare facility at a time period close to when the patient was diagnosed with the infectious disease.

Conventional EHRs suffer from various deficiencies with respect to notifying persons of potential exposure to an infectious disease. First, as noted above, a conventional EHR tends to require manual input from a healthcare worker as part of the process of notifying persons of potential exposure to the infectious disease. Second, even if the conventional EHR is configured with some version of an automatic notification system, the conventional EHR is not configured to notify persons who may have been exposed to the infectious disease that have already been discharged from the healthcare facility. Third, conventional EHRs tend to consider only room layouts in the healthcare facility when determining which persons in the healthcare facility have potentially been exposed to the infectious disease.

SUMMARY

The following is a brief summary of subject matter that is described in greater detail herein. This summary is not intended to be limiting as to the scope of the claims.

Disclosed herein are various technologies pertaining to transmitting notifications to computing devices of persons that may have been exposed to an infectious (i.e., contagious) disease in a healthcare facility. With more specificity, an improved electronic health records application (EHR) is disclosed herein. The EHR is a distributed application that includes both server-side functionality (server EHR) and client-side functionality (client EHR). The EHR is configured to generate and transmit notifications to computing devices of persons that have potentially been exposed to the infectious disease in the healthcare facility.

In operation, the server EHR executes on a server computing device and receives an indication that a patient in a healthcare facility has been diagnosed with an infectious disease at a datetime (i.e., a date and a time on the date). Responsive to receiving the indication, the server EHR determines first locations in the healthcare facility in which the patient was present within a time period that extends from the datetime to a predefined amount of time prior to the datetime. More specifically, the server EHR may maintain a record of positions of the patient (as well as other patients and healthcare workers) within the healthcare facility at different points in time (tracking data). The server EHR may execute a search over the tracking data based upon an identifier for the patient and an indication of the datetime. The search produces search results including the first locations in the healthcare facility in which the patient was present prior to being diagnosed with the infectious disease.

The server EHR also identifies portions of a heating, ventilating, and air conditioning (HVAC) system of the healthcare facility based upon the first locations. The portions of the HVAC system connect the first locations in the healthcare facility to second locations in the healthcare facility. The server EHR identifies the second locations based upon the first locations and the portions of the HVAC system.

The server EHR then identifies a person based upon at least one of the indication that the patient was diagnosed with the infectious disease at the datetime, the first locations, the second locations, or the portions of the HVAC system. In other words, the server EHR determines that the person has been present in at least one of the first locations or the second locations within the time period immediately prior to the datetime on which the patient was diagnosed with the infectious disease. In an example, the person may be a second patient of the healthcare facility. In another example, the person may be a healthcare worker who works in the healthcare facility. Hence, the person has potentially been exposed to the infectious disease. The server EHR may identify the person by executing a search over the tracking data based upon at least one of identifiers for the first locations, identifiers for the second locations, and the time period. The search produces search results including an identifier for the person, and the server EHR identifies the person based upon the search results. Importantly, the person may be a former patient who was present in the healthcare facility with the patient, but who was discharged from the healthcare facility prior to the patient being diagnosed with the infectious disease.

The server EHR then causes a notification to be transmitted to a computing device operated by the person. In an example, the notification may be an email message or a text message. The notification comprises an identifier for the infectious disease, an indication of the time period, and information about the infectious disease. The notification may advise the person to seek medical attention. The computing device may receive the notification and present the notification to the person on a display of the computing device.

The server EHR may also generate a heat map based upon the first locations, the second locations, and the portions of the HVAC system. The heat map comprises a first representation of the first locations and a second representation of the second locations. At least one of the first representation or the second representation are marked with one or more visual indicators. The one or more visual indicators are reflective of a likelihood that persons in the first locations or the second locations have been exposed to the infectious disease. The server EHR may transmit the heat map to a client electronic health records application (client EHR) executing on a client computing device that is in network communication with the server computing device. The client EHR may then present the heat map on a display of the client computing device.

The above-described technologies present various advantages over conventional EHRs. First, the EHR described above automatically notifies persons of potential exposure to an infectious disease, thus obviating a need for the EHR to receive manual input from a healthcare worker in order to notify the persons of their potential exposure to the infectious disease. Second, unlike conventional EHRs, the EHR described above can notify persons of potential exposure to the infectious disease who have been discharged from a healthcare facility prior to a patient being diagnosed with the infectious disease. Third, the EHR described above can more accurately predict exposure of the persons to the infectious disease by utilizing HVAC data of the healthcare facility.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

DETAILED DESCRIPTION

Figure 1:
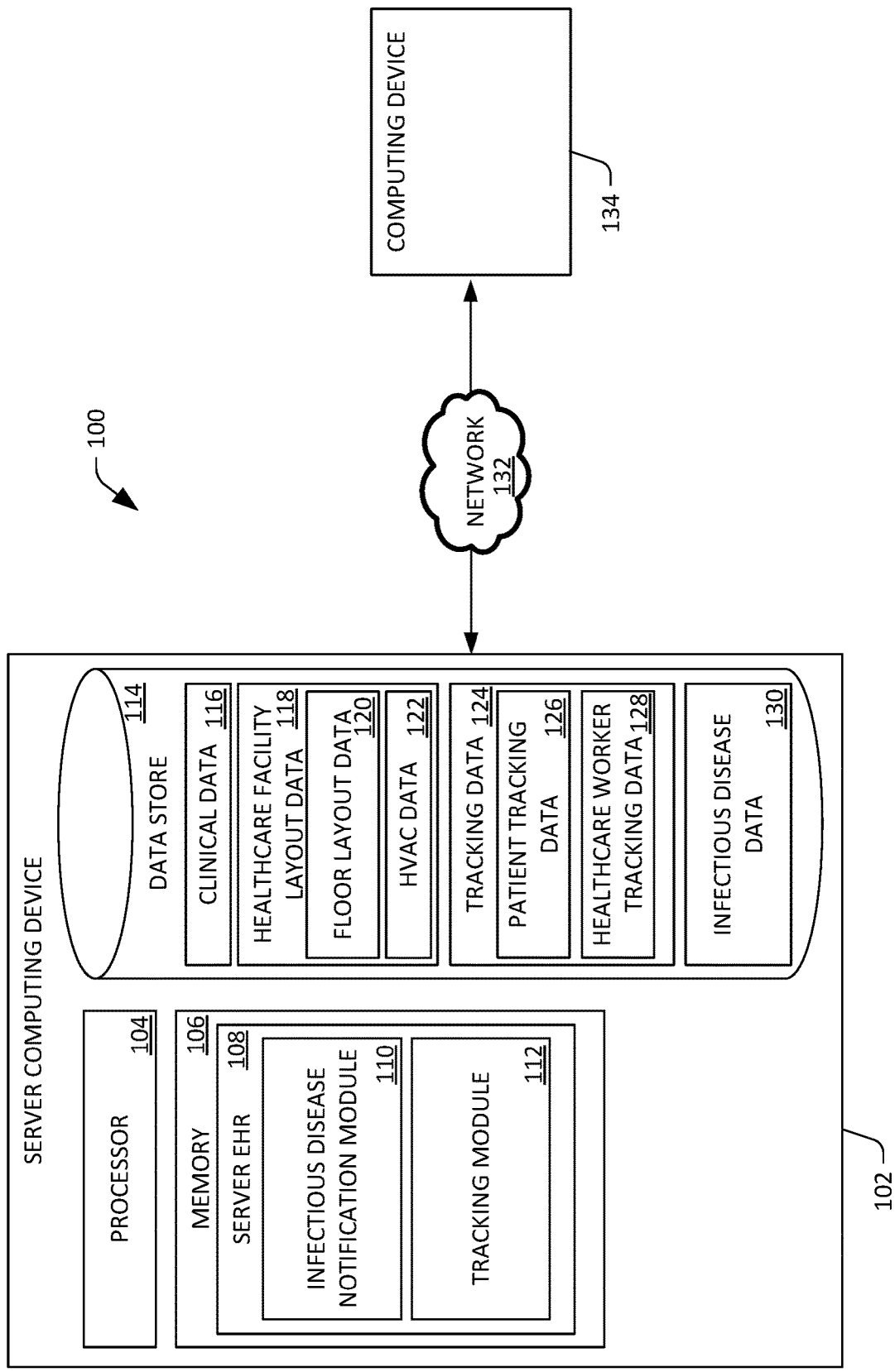
FIG. 1 is a functional block diagram of an exemplary computing system that facilitates notifying persons of potential exposure to an infectious disease.

Various technologies pertaining to notifying persons of potential exposure to an infectious disease via electronic means are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

With reference to FIG. 1, an exemplary computing system 100 that facilitates notifying persons of potential exposure to an infectious disease is illustrated. The computing system 100 includes a server computing device 102. The server computing device 102 comprises a processor 104 and memory 106, wherein the memory 106 has a server electronic health records application (server EHR) 108 loaded therein. The server EHR 108 is generally configured to perform a variety of tasks related to patient healthcare in a healthcare facility (e.g., patient intake, prescription generation, patient record creation and maintenance, etc.).

The server EHR 108 comprises an infectious disease notification module 110 and a tracking module 112. As will be described in greater detail below, the infectious disease notification module 110 is configured to determine identities of persons who have potentially been exposed to an infectious disease. The infectious disease notification module 110 is also configured to cause notifications to be sent to computing devices operated by the persons who have potentially been exposed to the infectious disease. Furthermore, the infectious disease notification module 110 may be configured to generate heat maps of potential exposure of persons in the healthcare facility to the infectious disease.

The tracking module 112 is configured to track locations of persons in a healthcare facility as the persons move about the healthcare facility. For instance, as will be described in greater detail below, the tracking module 112 may track locations of healthcare workers and/or patients within the healthcare facility based upon identifiers emitted from RFID tags embedded in devices that are worn or carried by the healthcare workers and/or the patients.

The server computing device 102 may further comprise a data store 114. The data store 114 may comprise clinical data 116 about patients, healthcare facility layout data 118, tracking data 124, and infectious disease data 130.

The clinical data 116 can include electronic health records, prescription records, claims data, patient/disease registries data, health surveys data, and/or clinical trials data.

The healthcare facility layout data 118 comprises a layout of a healthcare facility. As such, the healthcare facility layout data 118 includes floor layout data 120 and heating, ventilation, and air conditioning (HVAC data) 122. The floor layout data 120 comprises layouts of each floor of the healthcare facility. For instance, for a floor in the healthcare facility, the floor layout data 120 may include a representation of rooms on the floor and how the rooms connect to one another. The HVAC data 122 comprises a layout of the HVAC system of the healthcare facility. For instance, the HVAC data 122 may indicate which locations in the healthcare facility are connected via ventilation shafts. The HVAC data 122 may also include historical operating data for the HVAC system. For instance, the historical operating data may include time periods during which the HVAC system (or portions of the HVAC system) were operating and/or an intensity level at which portions of the HVAC system operated.

The tracking data 124 comprises locations of persons in the healthcare facility at different points in time. The server EHR 108 may search the tracking data 124 on both a person and/or a time period basis. In an example, the server EHR 108 may determine a location of a person in the healthcare facility at a datetime by executing a search over the tracking data 124 based upon an identifier for the person and an indication of the datetime. In another example, the server EHR 108 may determine identities of persons who were present in the location in the healthcare facility at the datetime by executing a search over the tracking data 124 based upon an identifier for the location and an indication of the datetime.

More specifically, the tracking data 124 may comprise patient tracking data 126 and healthcare worker tracking data 128. The patient tracking data 126 comprises locations of patients in the healthcare facility at different datetimes. In a non-limiting example, the patient tracking data 126 may indicate that a patient was present in an emergency room of the healthcare facility at a first datetime and was present in an intensive care unit of the healthcare facility at a second datetime. The healthcare worker tracking data 128 comprises locations of healthcare workers (e.g., physicians, nurses, janitorial workers, support staff, etc.) in the healthcare facility at the different datetimes. In a non-limiting example, the healthcare worker tracking data 128 may indicate that a healthcare worker was present in the emergency room of the healthcare facility at the first datetime and was present in the intensive care unit of the healthcare facility at the second datetime.

In an embodiment, persons (e.g., patients and/or healthcare workers) in the healthcare facility may be assigned devices (e.g., badges) having radio frequency identification (RFID) tags embedded therein. The persons may carry the device, wear the device, etc. Locations (e.g., rooms, hallways, etc.) within the healthcare facility may have RFID readers contained therein that are in communication with the tracking module 112 of the server EHR 108. In an example, a person in the healthcare facility may wear the badge having an RFID tag embedded therein. The RFID tag emits an identifier for the person. Thus, as the person moves about the healthcare facility, the RFID tag emits the identifier for the person which is read by the RFID readers. The RFID readers may communicate the identifier for the person, an indication of the datetime at which the identifier for the person was read, and identifiers for the locations of the RFID readers to the tracking module 112. The tracking module 112 may then cause such data to be stored as part of the tracking data 124. Hence, the tracking data 124 may be based upon the identifier for the person emitted from the RFID tag.

In an embodiment, the tracking data 124 may be based upon room assignment data of patients in the healthcare facility and/or schedules of healthcare workers working in the healthcare facility. In an example, the tracking data 124 may be based upon known travel paths to rooms in the healthcare facility and datetime in which patients were checked into the healthcare facility.

The infectious disease data 130 comprises information about infectious diseases. For example, the infectious disease data 130 may comprise identifiers for infectious diseases, symptoms of the infectious diseases, modes of transmission of the infectious diseases, treatment advice for the infectious diseases, etc.

Although not depicted in FIG. 1, the data store 114 may also comprise contact information (e.g., phone numbers, email addresses, etc.) for patients of the healthcare facility and healthcare workers working at the healthcare facility.

The computing system 100 further includes a computing device 134 operated by a person. The computing device 134 may be in communication with the server computing device 102 (or another intermediary computing device) by way of a network 132 (e.g., the Internet, intranet, etc.). As will be described in greater detail below, the computing device 134 may be a client computing device operated by a healthcare worker and/or a patient computing device operated by a patient.

Figure 2:
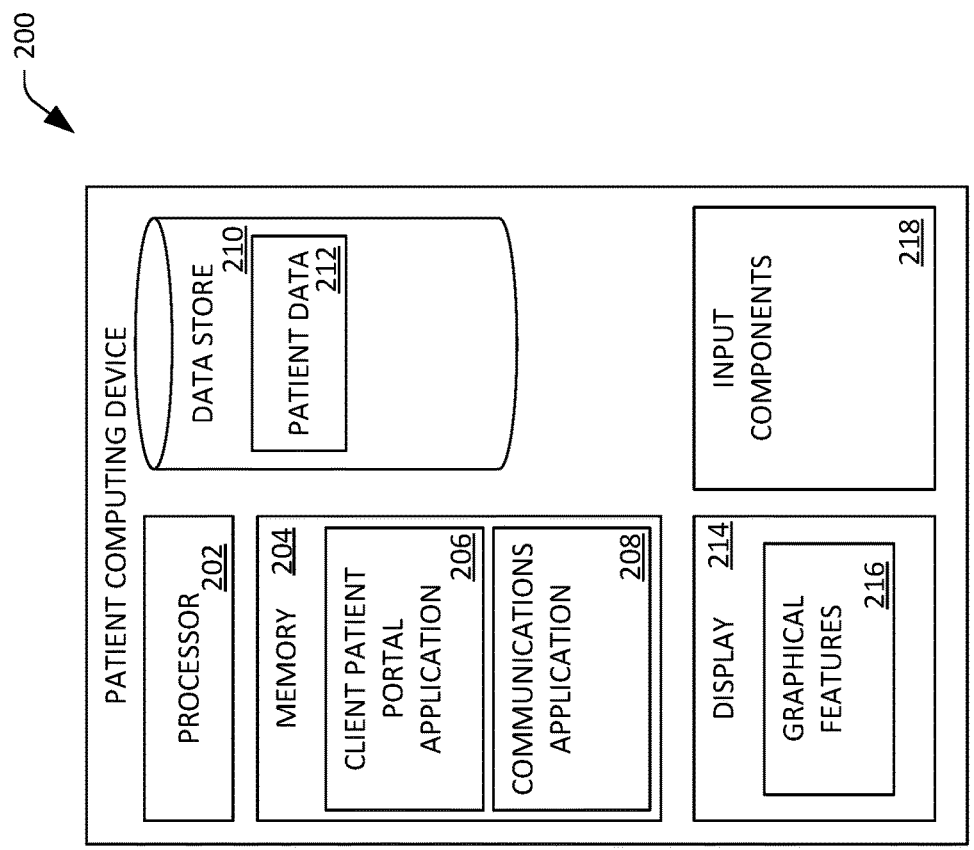
FIG. 2 is a functional block diagram of an exemplary patient computing device.

Referring now to FIG. 2, an exemplary patient computing device 200 operated by a patient is depicted. The patient computing device 200 may be or include the computing device 134 and/or the computing device 134 may be or include the computing device 200. In a non-limiting example, the patient computing device 200 may be a smartphone, a tablet computing device, a wearable computing device such as a smartwatch, a laptop computing device, or a desktop computing device.

The patient computing device 200 includes a processor 202 and memory 204 wherein the memory 204 may have a client patient portal application 206 and/or a communications application 208 loaded therein. In general, the client patient portal application 206 (when executed by the processor 202) is configured to interface with a server patient portal application to allow the patient to access his or her health data that is maintained by the server patient portal application (described in greater detail below). The communications application 208 (when executed by the processor 202) is configured to receive and transmit communications from/to other computing devices. For instance, the communications application 208 may be a text messaging application, an email application, etc.

The patient computing device 200 may also include a data store 210 comprising patient data 212 (as well as other data) about the patient, wherein the patient data 212 is a subset of the clinical data 116 retained in the data store 114 of the server computing device 102. The patient computing device 200 may include a display 214, whereupon graphical features 216 may be presented thereon. For instance, a notification that the patient may have been exposed to an infectious disease may be presented as part of the graphical features 216. Furthermore, the patient computing device 200 may include input components 218 suitable for data input. For instance, the input components 218 may include a touchscreen, a mouse, a keyboard, a trackpad, a scroll wheel, a microphone, a camera, and/or a video camera.

Figure 3:
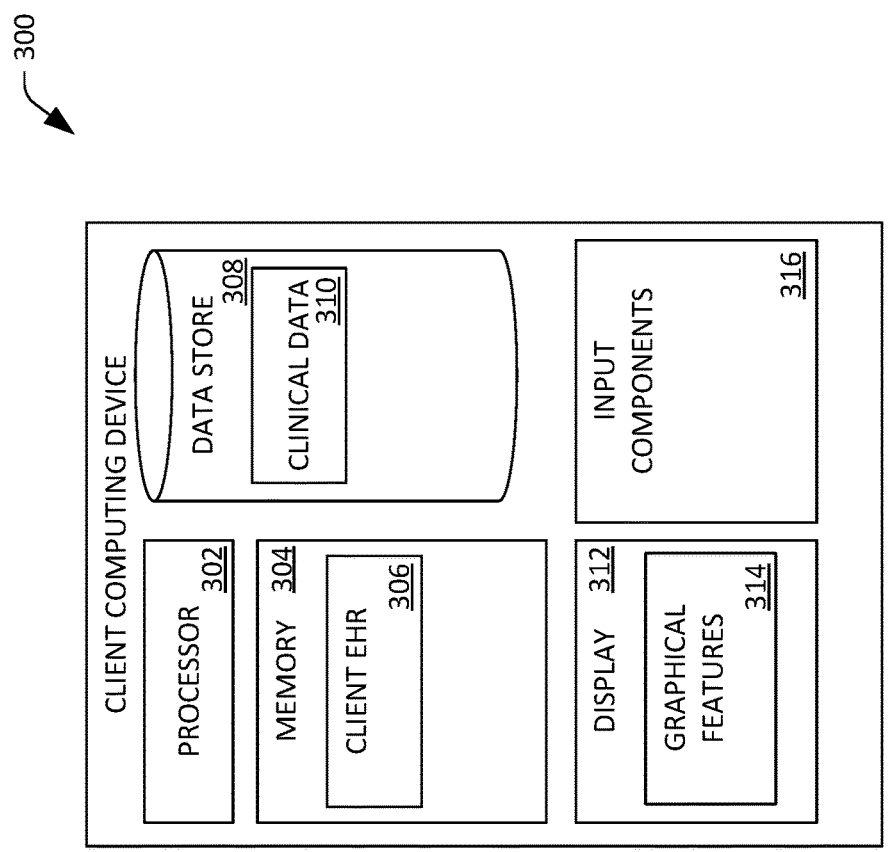
FIG. 3 is a functional block diagram on an exemplary client computing device.

Turning now to FIG. 3, an exemplary client computing device 300 operated by a healthcare worker is depicted. The client computing device 300 may be or include the computing device 134 and/or the computing device 134 may be or include the computing device 300. In a non-limiting example, the client computing device 300 may be a smartphone, a tablet computing device, a wearable computing device such as a smartwatch, a laptop computing device, or a desktop computing device.

The client computing device 300 includes a processor 302 and memory 304, wherein the memory 304 has a client electronic health records application (client EHR) 306 loaded therein. In general, the client EHR 306 is configured to interface with the server EHR 108 executing on the server computing device 102, thereby providing the healthcare worker with access to functionality of the server EHR 108.

The client computing device 300 may include a data store 308 comprising clinical data 310 about patients. It is understood that there may be overlap between the clinical data 310 stored in the data store 308 and the clinical data 116 stored in the data store 114 of the server computing device 102. The client computing device 300 may include a display 312, whereupon graphical features 314 may be presented thereon. For instance, a notification that the healthcare worker may have been exposed to an infectious disease may be presented as part of the graphical features 314. Furthermore, the patient computing device 300 may include input components 316 suitable for data input. For instance, the input components 316 may include a touchscreen, a mouse, a keyboard, a trackpad, a scroll wheel, a microphone, a camera, and/or a video camera.

Operation of the computing system 100 is now set forth. It is contemplated that a patient in a healthcare facility has been diagnosed with an infectious (i.e., contagious) disease. In an example, the patient may have been present in different locations of the healthcare facility (e.g., a waiting room, a treatment room, etc.) prior to being diagnosed with the infectious disease.

The server EHR 108 receives an indication that the patient in the healthcare facility has been diagnosed with the infectious disease at a datetime (i.e., a date and a time on the date). For instance, the server EHR 108 may receive the indication (including an identifier for the patient) from a client EHR executing on a client computing device operated a healthcare worker. Responsive to receiving the indication, the server EHR 108 (by way of the infectious disease notification module 110) determines, based upon the indication, first locations in the healthcare facility in which the patient was present within a time period that extends from the datetime to a predefined amount of time prior to the datetime. In a non-limiting example, the first locations in the healthcare facility may include an emergency room and an intensive care unit and the time period may range from 1 to 6 hours, 6 to 24 hours, 24 to 48 hours, etc.

The infectious disease notification module 110 of the server EHR 108 may determine the first locations in the healthcare facility by executing a search over the tracking data 124 (more specifically, the patient tracking data 126). The search may be based upon an identifier for the patient, as well as an indication of the datetime on which the patient was diagnosed with the infectious disease and the time period. The search produces search results, wherein the search results include identifiers for the first locations in the healthcare facility. Thus, the infectious disease notification module 110 may determine the first locations in the healthcare facility based upon the search results.

The infectious disease notification module 110 of the server EHR 108 then identifies portions of an HVAC system of the healthcare facility based upon the first locations. The portions of the HVAC system connect the first locations in the healthcare facility to second locations in the healthcare facility. For instance, the portions of the HVAC system may be ventilation shafts that connect the first locations to the second locations. The infectious disease notification module 110 may identify the portions of the HVAC system by executing a search over the HVAC data 122 based upon identifiers for the first locations. The search produces search results, wherein the search results include identifiers for the portions of the HVAC system, as well as identifiers for the second locations. Thus, the infectious disease notification module 110 determines the portions of the HVAC based upon the search results. The infectious disease notification module 110 also determines the second locations in the healthcare facility based upon the portions of the HVAC system.

The infectious disease notification module 110 of the server EHR 108 then identifies a person that may have been exposed to the infectious disease in the healthcare facility. The person may be a second patient or a healthcare worker, such as a physician, a nurse, a maintenance worker, or any other person who works at the healthcare facility. The infectious disease notification module 110 of the server EHR 108 determines that the person has been present in at least one of the first locations or the second locations within the time period. Importantly, in the event that the person is the second patient, the second patient may have been discharged from the healthcare facility prior to the datetime at which the patient was diagnosed with the infectious disease. Thus, the server EHR 108 (by way of the infectious disease notification module 110) may notify the second patient of potential exposure to the infectious disease despite the second patient no longer being present in the healthcare facility.

The infectious disease notification module 110 of the server EHR 108 may identify the person based upon at least one of the indication that the patient was diagnosed with the infectious disease at the datetime, the first locations, the second locations, or the portions of the HVAC system. More specifically, the infectious disease notification module 110 may execute a search over the tracking data 124 based upon an indication of the time period that extends from the datetime to the predefined amount of time prior to the datetime, identifiers for the first locations, and identifiers for the second locations. The search produces search results, wherein the search results include an identifier for the person. The infectious disease notification module 110 may ascertain contact information for the person (e.g., a phone number, an email address, etc.) based upon the identifier for person.

The infectious disease notification module 110 of the server EHR 108 may determine the information about the infectious disease by executing a search over the infectious disease data 130 based upon the identifier for the infectious disease. The search produces search reduces, wherein the search results include the information about the infectious disease. As mention above, the information about the infectious disease may include a transmission type (e.g., airborne, droplet, physical contact, etc.) of the infectious disease. The infectious disease notification module 110 may identify the person based further upon the transmission type of the infectious disease.

It is understood that operation of the HVAC system of the healthcare facility may affect transmission of the infectious disease. As such, in an embodiment, the server EHR 108 (by way of the infectious disease notification module 110) may further identify the person based upon historical operating data for the HVAC system comprised by the HVAC data 122. The historical operating data may comprise time periods during which the portions of the HVAC system were operating (e.g., time periods when air was flowing from the first locations to the second locations via the portions of the HVAC system, or vice versa). The historical operating data may also comprise an intensity level at which the portions of the HVAC system operated during the time periods.

The infectious disease notification module 110 of the server EHR 108 then causes a notification to be transmitted to the computing device 134 operated by the person. As such, the infectious disease notification module 110 may generate the notification and transmit the notification to the computing device 134 (by using the contact information for the person). The notification includes an identifier for the infectious disease, an indication of the time period that extends from the datetime to the predefined amount of time prior to the datetime, and the information about the infectious disease. The notification may be configured such that the notification is free from any protected health information of the patient who has been diagnosed with the infectious disease. The notification may advise the person to seek medical attention. In an embodiment, the notification may be a short message server (SMS) text message. In another embodiment, the notification may be an email message.

In an embodiment, the infectious disease notification module 110 of the server EHR 108 may transmit the notification to a second server computing device (not shown), and the second server computing device may transmit the notification to the computing device 134. In another embodiment, the infectious disease notification module 110 may transmit the notification directly to the computing device 134. As discussed above, when the person is a second patient, the computing device 134 may be the patient computing device 200 operated by the second patient. When the person is a healthcare worker, the computing device 134 may be the client computing device 300 operated by the healthcare worker.

Responsive to receiving the notification, the computing device 134 may present the notification to the person on a display of the computing device 134. The person may then view the notification.

The infectious disease notification module 110 of the server EHR 108 may also generate a heat map based upon the first locations in the healthcare facility, the second locations in the healthcare facility, and the portions of the HVAC system. The heat map comprises a first representation of the first locations (e.g., a two-dimensional map) and a second representation of the second locations. At least one of the first representation or the second representations are marked with one or more visual indicators. The one or more visual indicators are reflective of a likelihood that persons in the first locations and/or the second locations have been exposed to the infectious disease. The one or more visual indicators may be placed on the heat map based upon the transmission type of the infectious disease. The server EHR 108 (by way of the infectious disease notification module 110) may transmit the heat map to a client electronic health records application executing on a client computing device operated by a healthcare worker. The client EHR may then present the heat map on a display of the client computing device, whereupon the heat map may be viewed by the healthcare worker.

In an embodiment, the infectious disease notification module 110 of the server EHR 108 may determine locations in the healthcare facility in which the infectious disease appear to originate. For example, the infectious disease notification module 110 may receive an indication that a second patient in the healthcare facility has been diagnosed with the infectious disease at a second datetime (i.e., a different datetime than the datetime discussed above). Using an approach similar to that described above, the infectious disease notification module 110 may determine that the second patient was also present in the first locations at the second datetime. The infectious disease notification module 110 may then mark the first locations for review by a healthcare worker in the healthcare facility layout data 118. The healthcare worker may then examine the first locations to determine if any preventative measures can be implemented to reduce risk of the occurrence of the infectious disease.

In an embodiment where the person is a second patient, the infectious disease notification module 110 of the server EHR 108 may cause a second notification to be generated and transmitted to a computing device operated by a clinician (e.g., a primary care physician) of the second patient. The second notification may comprise an identifier for the second patient, contact information for the second patient, an identifier for the infectious disease, an indication of the time immediately prior to the datetime, and information about the infectious disease. Using the contact information, the clinician may then contact the second patient and advise them about the infectious disease.

In an embodiment where the person is a second patient, the infectious disease notification module 110 of the server EHR 108 may utilize clinical data for the second patient in deciding whether to transmit a notification to the second patient. For instance, subsequent to identifying the second patient, the infectious disease notification module 110 may retrieve clinical data for the second patient by executing a search over the clinical data 116 based upon an identifier for the second patient. When the clinical data for the second patient indicates that the second patient has a low risk for being infected with the infectious disease (e.g., the infectious disease is common influenza, the second patient was located several beds away from the patient, the second patient has received an influenza immunization shot, the second patient is a healthy 23 year old, etc.), the infectious disease notification module 110 may fail to notify the second patient. When the clinical data for the second patient indicates that the second patient has a right risk for being infected with the infectious disease (e.g., the infectious disease is common influenza, the second patient was located in a bed next to the patient, the second patient has not received an influenza immunization shot, the second patient is a sick 85 year old, etc.), the infectious disease notification module 110 may generate and transmit the notification described above. Additionally, the notification may include a request that the second patient return to the healthcare facility for monitoring.

Although the above-described process has been described as identifying a single person who may have been exposed to the infectious disease, it is to be understood that the above-described process may identify many persons who are currently (or previously) in the healthcare facility that may have been exposed to the infectious disease. Additionally, although the above-described process has been described as involving a single infectious disease, it is to be understood that the above-described process may be utilized for many different infectious diseases. Furthermore, although the above-described processes have been described as being performed by the infectious disease notification module 110 of the server EHR 108, it is to be understood that the server EHR 108 may perform the above-described functionality.

Figure 4:
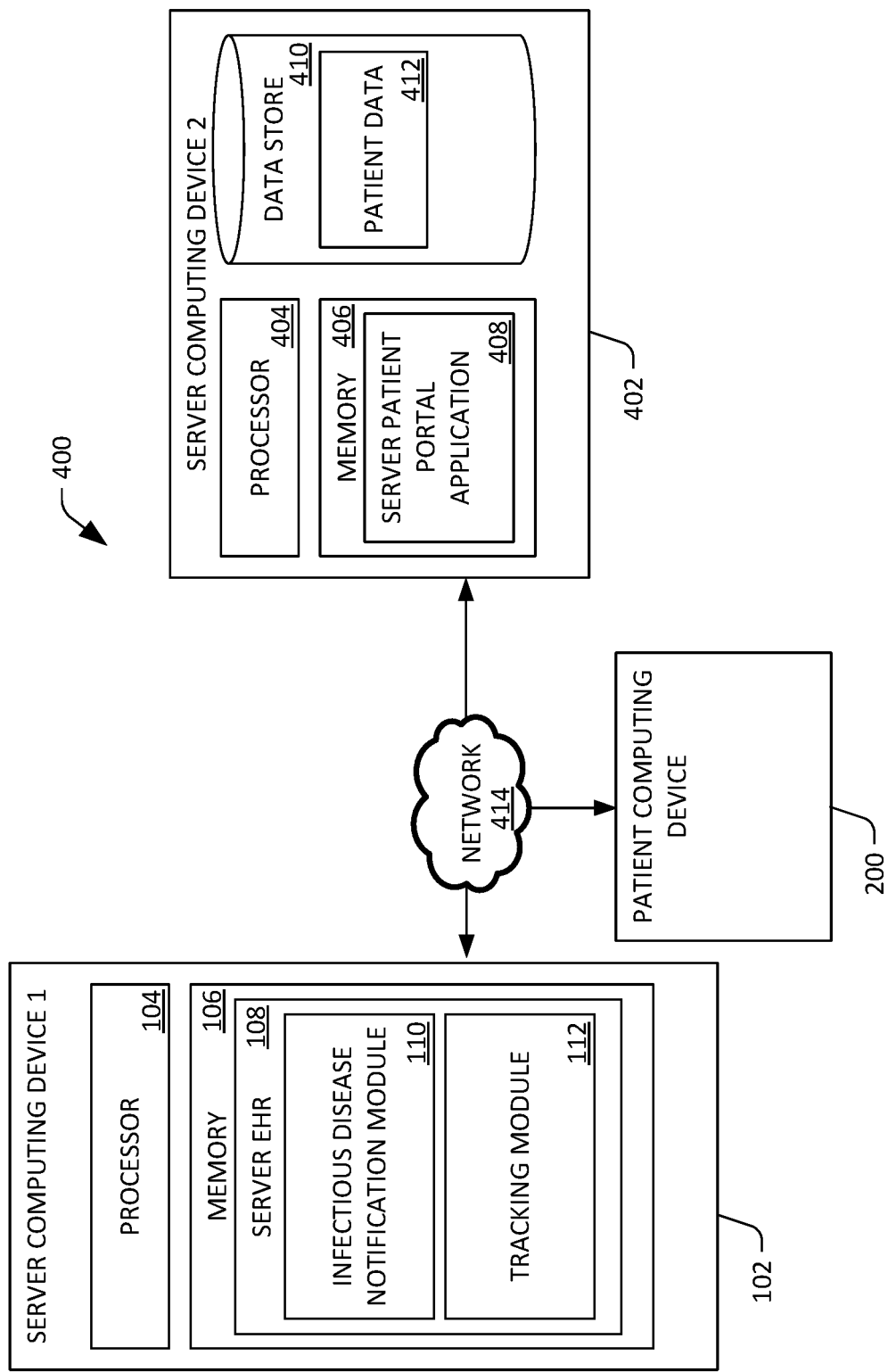
FIG. 4 is a functional block diagram of an exemplary computing system that facilitates notifying persons of potential exposure to an infectious disease.

With reference to FIG. 4, an exemplary computing system 400 that facilitates notifying persons of potential exposure to an infectious disease is illustrated is illustrated. The computing system 400 includes the server computing device 102 (referred to now as "the first server computing device 102" for clarity) described above in the description of FIG. 1. Although not depicted in FIG. 4, it is to be understood that the first server computing device 102 comprises all of the components described above in the description of FIG. 1 (e.g., the data store 114, the healthcare facility layout data 118, the tracking data 124, etc.).

The computing system 400 additionally includes the patient computing device 200 described above in the description of FIG. 2. The patient computing device 200 is operated by a (second) patient who is different than the patient who is diagnosed with an infectious disease.

The computing system 400 further includes a second server computing device 402 that is in communication with the first server computing device 102 by way of a network 414 (e.g., the Internet, intranet, etc.). The second server computing device 402 is also in communication with the patient computing device 200 by way of the network 414 (or another network). The second server computing device 402 comprises a processor 404 and memory 406, wherein the memory 406 has a server patient portal application 408 loaded therein. In general, the server patient portal application 408 (when executed by the processor 404) is configured to allow a patient to access his or her health data, including prescription medications, health records, communications with healthcare providers, input self-reported patient health data, etc. The patient may access functionality of the server patient portal application 408 by way of the client patient portal application 206 executing on the patient computing device 200.

The second server computing device 402 may include a data store 410. The data store 410 may comprise patient data 412 about patients, wherein the patient data 412 is a subset of the clinical data 116 retained in the data store 114 of the first server computing device 102. The server EHR 108 is configured to provide the server patient portal application 408 with the patient data 412, wherein an administrator of the server EHR 108 can set forth policies as to what data is included in the patient data 412 (and the format of such data).

Operation of the computing system 400 is now set forth. The computing system 400 operates in a manner similar to that of the computing system 100. For instance, the infectious disease notification module 110 of the server EHR 108 receives an indication that a first patient in a healthcare facility has been diagnosed with an infectious disease at a datetime and determines first locations in the healthcare facility in which the first patient was present within a time period that extends from the datetime to a predefined amount of time prior to the datetime. The infectious disease notification module 110 identifies portions of the HVAC system connecting the first locations to second locations in the healthcare facility. The infectious disease notification module 110 identifies a second patient based upon at least one of the first locations, the second locations, the portions of the HVAC system, and the time period. The infectious disease notification module 110 determines that the second patient has been present in at least one of the first locations or the second locations within the time period.

However, in the computing system 400, the server EHR 108 (by way of the infectious disease notification module 110) transmits a notification (described above in the description of operation of the computing system 100) to the server patient portal application 408 executing on the second server computing device 402. The server patient portal application 408 then transmits the notification to the client patient portal application 206 executing on the patient computing device 200 operated by the second patient. The client patient portal application 206 then presents the notification to the second patient on a graphical user interface (GUI) for the client patient portal application 206 presented on the display 214 of the patient computing device 200.

Figure 5:
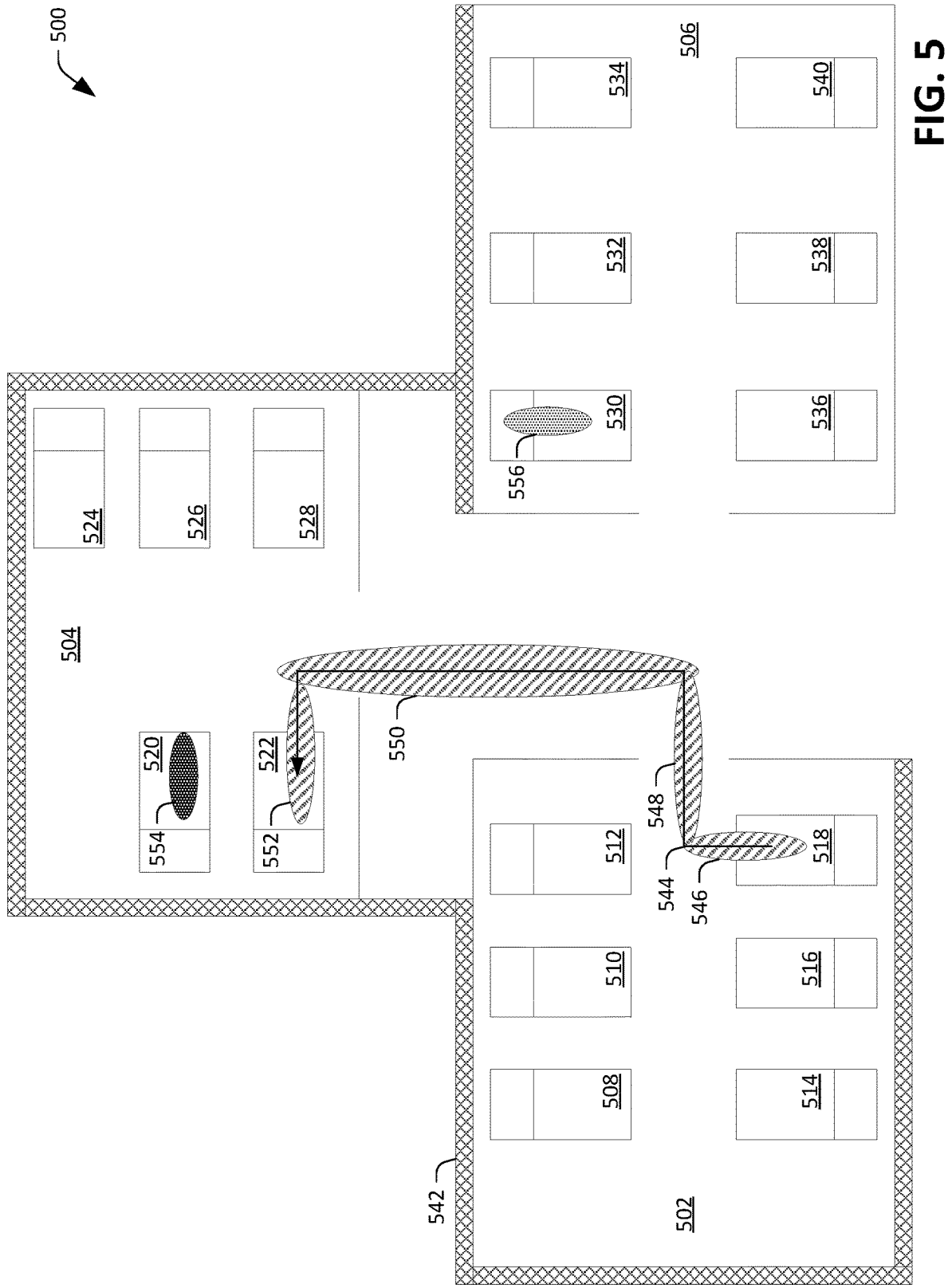
FIG. 5 is a depiction of a heat map.

Turning now to FIG. 5, an exemplary heat map 500 is illustrated. In an example, the heat map 500 may be presented on the display 312 of the client computing device 300. As shown in FIG. 5, the heat map 500 includes a depiction of a first room 502, a second room 504, and a third room 506. The first room 502 comprises first beds 508-518, some or all of which may be occupied by patients. The second room 504 comprises second beds 520-528, some or all which may be occupied by patients. The third room 506 comprises third beds 530-540, some or all of which may be occupied by patients. The heat map 500 may include a depiction of a portion of the HVAC system 542. As shown in FIG. 5, the portion of the HVAC system 542 connects the first room 502 to the second room 504 and the third room 506.

In the example shown in FIG. 5, a patient (not shown) is moved from bed 518 in the first room 502 to bed 522 in the second room 504 along a path 544. Subsequently, the patient is diagnosed with an infectious disease. As such, the heat map 500 includes visual indicators 546-556 that are reflective of a likelihood that persons in a location represented by the heat map has been exposed to the infectious disease. For example, as the bed 520 is adjacent to the bed 522 in which the patient was placed, the visual indicator 554 may have a first intensity to depict a higher likelihood that a second patient in the bed 520 has been exposed to the infectious disease. In another example, as the patient has not been entered the third room 506, the visual indicator 556 may have a second intensity to depict a lower likelihood that a third patient in the bed 530 has been exposed to the infectious disease.

Figure 6:
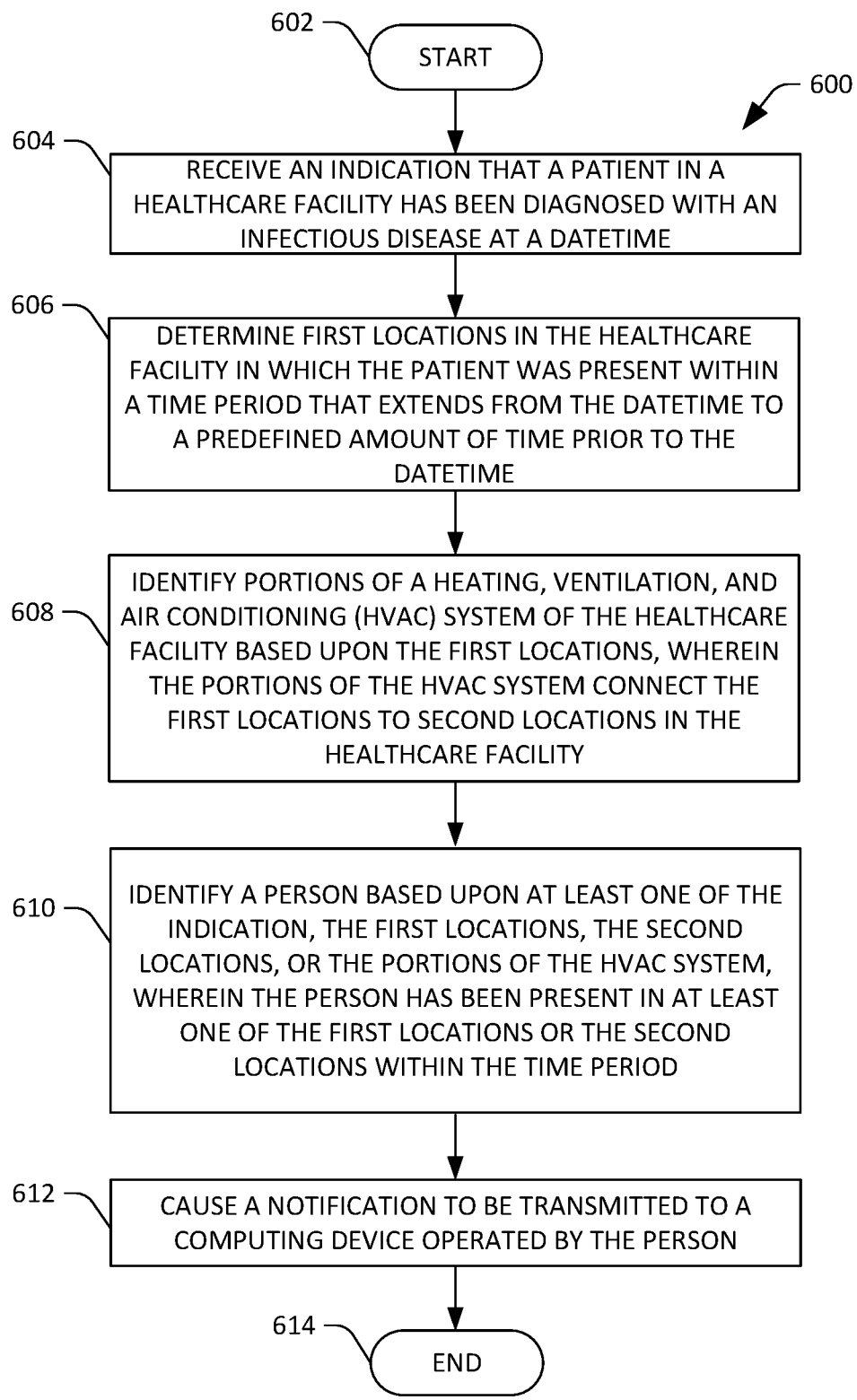
FIG. 6 is a flow diagram that illustrates an exemplary methodology performed by a server computing device for notifying persons of potential exposure to an infectious disease.
Figure 7:
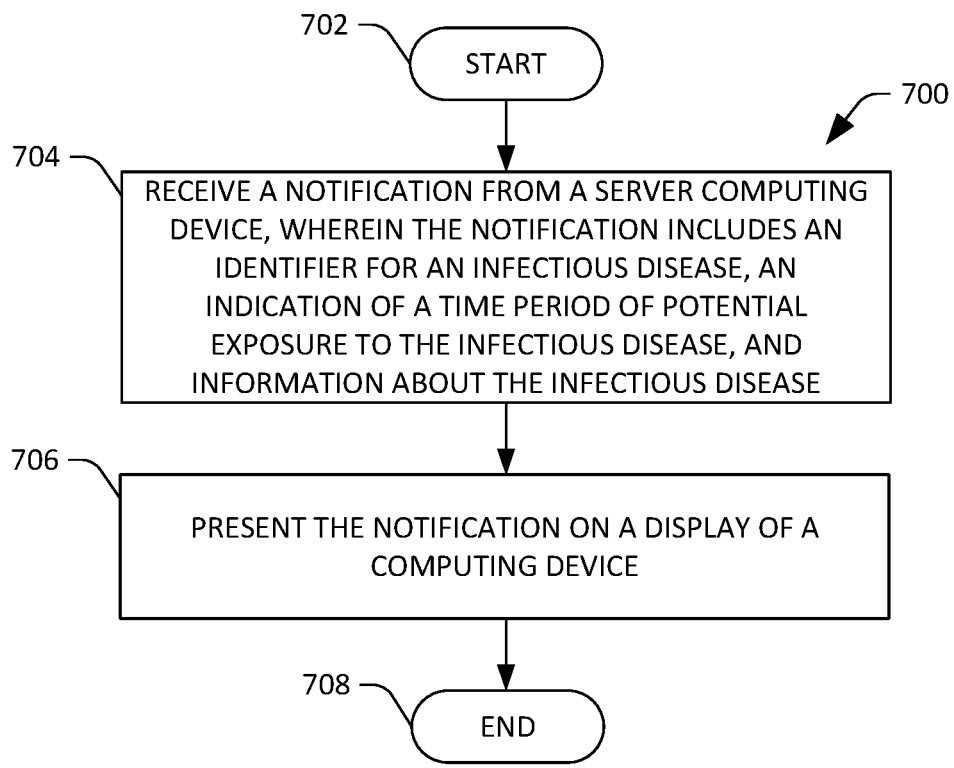
FIG. 7 is a flow diagram that illustrates an exemplary methodology performed by a computing device for presenting a notification to a person potentially exposed to an infectious disease.

FIGS. 6 and 7 illustrate exemplary methodologies relating to notifying patients of potential exposure to an infectious disease. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 6, a methodology 600 performed by a server computing device that facilitates notifying patients of potential exposure to an infectious disease is illustrated. The methodology 600 begins at 602, and at 604, the server computing device receives an indication that a patient in a healthcare facility has been diagnosed with an infectious disease at a datetime. At 606, the server computing device determines, based upon the indication, first locations in the healthcare facility in which the patient was present within a time period that extends from the datetime to a predefined amount of time prior to the datetime. At 608, the server computing device identifies portions of a HVAC system of the healthcare facility based upon the first locations. The portions of the HVAC system connect the first locations in the healthcare facility to second locations in the healthcare facility. At 610, the server computing device identifies a person based upon at least one of the indications, the first locations, the second locations, or the portions of the HVAC system. The server computing device determines that the person has been present in at least one of the first locations or the second locations within the time period. Hence, the person may have been exposed to the infectious disease. As such, at 612, the server computing device causes a notification to be transmitted to a computing device operated by the person. The notification includes an identifier for the infectious disease, an indication of the time period, and information about the infectious disease. The methodology 600 concludes at 614.

Referring now to FIG. 7, a methodology 700 performed by a computing device that facilitates notifying a person of potential exposure to an infectious disease is illustrated. The methodology 700 begins at 702, and at 704, the computing device receives a notification from a server computing device. The notification includes an identifier for an infectious disease, a time period of potential exposure of the person to the infectious disease, and information about the infectious disease. At 706, the computing device presents the notification on a display of the computing device. The methodology 700 concludes at 708.

Figure 8:
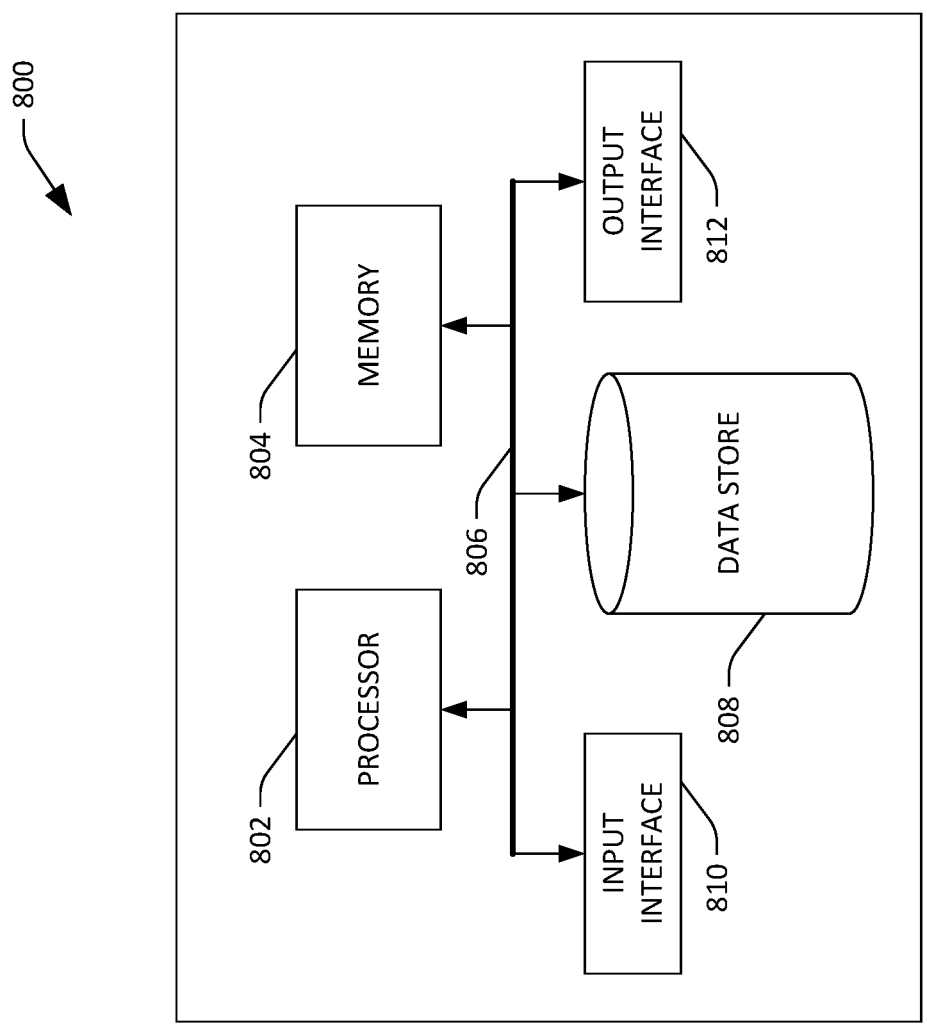
FIG. 8 is an exemplary computing system.

Referring now to FIG. 8, a high-level illustration of an exemplary computing device 800 that can be used in accordance with the systems and methodologies disclosed herein is illustrated. For instance, the computing device 800 may be used in a system that transmits a notification to a computing device operated by a person indicating that the person may have been exposed to an infectious disease. By way of another example, the computing device 800 can be used in a system that generates a heat map of potential exposure of persons in a healthcare facility to an infectious disease. The computing device 800 includes at least one processor 802 that executes instructions that are stored in a memory 804. The instructions may be, for instance, instructions for implementing functionality described as being carried out by one or more components discussed above or instructions for implementing one or more of the methods described above. The processor 802 may access the memory 804 by way of a system bus 806. In addition to storing executable instructions, the memory 804 may also store clinical data for patients, healthcare facility layout data (including floor layout data and HVAC data), tracking data (including patient tracking data and healthcare worker tracking data), infectious disease data, etc.

The computing device 800 additionally includes a data store 808 that is accessible by the processor 802 by way of the system bus 806. The data store 808 may include executable instructions, clinical data for patients, healthcare facility layout data (including floor layout data and HVAC data), tracking data (including patient tracking data and healthcare worker tracking data), infectious disease data. The computing device 800 also includes an input interface 810 that allows external devices to communicate with the computing device 800. For instance, the input interface 810 may be used to receive instructions from an external computer device, from a user, etc. The computing device 800 also includes an output interface 812 that interfaces the computing device 800 with one or more external devices. For example, the computing device 800 may display text, images, etc. by way of the output interface 812.

It is contemplated that the external devices that communicate with the computing device 800 via the input interface 810 and the output interface 812 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 800 in a manner free from constraints imposed by input devices such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 800 may be a distributed system. Thus, for instance, several devices may be in communication by way of a network connection and may collectively perform tasks described as being performed by the computing device 800.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FP- GAs), Application-specific Integrated Circuits (ASICs), Application-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A server computing device comprising:
   a processor; and
   memory storing a server electronic health records application (server EHR), wherein the server EHR, when executed by the processor, causes the processor to perform acts comprising:
     responsive to receiving an indication that a patient in a healthcare facility has been diagnosed with an infectious disease at a datetime, executing a first search over computer-readable tracking data stored in a computer-readable data store based upon an identifier for the patient, wherein the first search produces first search results, the first search results comprising first locations in the healthcare facility in which the patient was present within a time period that extends from the datetime to a predefined amount of time prior to the datetime;
     responsive to executing the first search, executing a second search over computer-readable healthcare facility layout data stored in the computer-readable data store based upon the first locations, wherein the second search produces second search results, the second search results comprising:
       portions of a heating, ventilation, and air conditioning (HVAC) system of the healthcare facility that connect the first locations in the healthcare facility to second locations in the healthcare facility; and
       historical operating data for the HVAC system, wherein the historical operating data for the HVAC system comprises time periods during which the of the HVAC system were operating such that air was flowing from the first locations to the second locations and an intensity level at which the portions of the HVAC system operated during the time periods;
     subsequent to executing the second search, executing a third search over the computer-readable tracking data stored in the computer-readable data store based upon the first locations, the second locations, and the time period in which the patient was present in the first locations in the healthcare facility to identify a person that has been potentially exposed to the infectious disease, wherein the server EHR determines that the person has potentially been exposed to the infectious disease based upon the historical operating data for the HVAC system; and
     causing a notification to be transmitted, over a network connection, to a computing device operated by the person, wherein the notification includes an identifier for the infectious disease, an indication of the time period, and information about the infectious disease, and further wherein the notification is presented on a display of the computing device.

2. The server computing device of claim 1, wherein the notification is a short message service (SMS) text message.

3. The server computing device of claim 1, wherein the person is a second patient, wherein the computing device executes a client patient portal application, wherein the computing device is in network communication with a second server computing device, wherein the second server computing device is in network communication with the server computing device, wherein the second server computing device executes a server patient portal application, wherein causing the notification to be transmitted to the computing device comprises:
   transmitting the notification to the server patient portal application, wherein the server patient portal application transmits the notification to the client patient portal application, wherein the client patient portal application presents the notification to the second patient on a graphical user interface (GUI) for the client patient portal application presented on the display of the computing device.

4. The server computing device of claim 1, the acts further comprising:
   generating a heat map based upon the first locations in the healthcare facility, the second locations in the healthcare facility, and the portions of the HVAC system, wherein the heat map comprises a first representation of the first locations and a second representation of the second locations, wherein at least one of the first representation or the second representation are marked with one or more visual indicators, wherein the one or more visual indicators are reflective of a likelihood that persons in the first locations or the second locations have been exposed to the infectious disease.

5. The server computing device of claim 4, the acts further comprising:
   transmitting the heat map to a client electronic health records application (client EHR) executing on a client computing device that is in network communication with the server computing device, wherein the client EHR presents the heat map on a display of the client computing device.

6. The server computing device of claim 1, wherein the person is a healthcare worker who works at the healthcare facility.

7. The server computing device of claim 1, wherein the identifier for the patient and the datetime are included in the indication.

8. The server computing device of claim 1, the acts further comprising:
   subsequent to executing the second search and prior to executing the third search, identifying the second locations based upon the first locations and the portions of the HVAC system.

9. The server computing device of claim 1, wherein the person was in at least one of the second locations during the time period.

10. The server computing device of claim 1, the acts further comprising:

receiving an indication that a second patient in the healthcare facility has been diagnosed with the infectious disease at a second datetime;

determining that the second patient has been present in the first locations within a second time period that extends from the second datetime to a second predefined amount of time prior to the second datetime; and marking the first locations for review by a healthcare worker.

11. The server computing device of claim 1, the acts further comprising:

prior to identifying the person, determining a transmission type of the infectious disease, wherein the transmission type is at least one:

airborne;

droplet; or physical contact, wherein identifying the person is further based upon the transmission type.

12. A method executed by a server computing device while a processor of the server computing device executes a server electronic health records application (server EHR), the method comprising:

receiving an indication that a patient in a healthcare facility has been diagnosed with an infectious disease at a datetime;

executing a first search over computer-readable tracking data stored in a computer-readable data store based upon an identifier for the patient, wherein the first search produces first search results, the first search results comprising first locations in the healthcare facility in which the patient was present within a time period that extends from the datetime to a predefined amount of time prior to the datetime;

responsive to executing the first search, executing a second search over computer-readable healthcare facility layout data stored in the computer-readable data store based upon the first locations, wherein the second search produces second search results, the second search results comprising:

portions of a heating, ventilation, and air conditioning (HVAC) system of the healthcare facility that connect the first locations in the healthcare facility to second locations in the healthcare facility; and historical operating data for the HVAC system, wherein the historical operating data for the HVAC system comprises time periods during which the portions of the HVAC system were operating such that air was flowing from the first locations to the second locations and an intensity level at which the portions of the HVAC system operated during the time periods;

subsequent to executing the second search, executing a third search over the computer-readable tracking data stored in the computer-readable data store based upon the first locations, the second locations, and the time period in which the patient was present in the first locations in the healthcare facility to identify a person that has been potentially exposed to the infectious disease, wherein the server EHR determines that the person has potentially been exposed to the infectious disease based upon the historical operating data for the HVAC system; and causing a notification to be transmitted, over a network connection, to a computing device operated by the person, wherein the notification includes an identifier for the infectious disease, an indication of the time period, and information about the infectious disease, and further wherein the notification is presented on a display of the computing device.

13. The method of claim 12 further comprising:

generating a heat map based upon the first locations in the healthcare facility, the second locations in the healthcare facility, and the portions of the HVAC system, wherein the heat map comprises a first representation of the first locations and a second representation of the second locations, wherein at least one of the first representation or the second representation are marked with one or more visual indicators, wherein the one or more visual indicators are reflective of a likelihood that persons in the first locations or the second locations have been exposed to the infectious disease; and transmitting the heat map to a client electronic health records application (client EHR) executing on a client computing device that is in network communication with the server computing device, wherein the client EHR presents the heat map on a display of the client computing device.

14. The method of claim 12, wherein the patient is assigned a device having a radio frequency identification (RFID) tag embedded therein, wherein RFID readers in the healthcare facility track locations of the patient in the healthcare facility as the patient moves about the healthcare facility based upon an identifier for the patient emitted from the RFID tag, wherein determining the first locations in the healthcare facility is based upon the identifier for the patient emitted from the RFID tag.

15. The method of claim 12, further comprising:

subsequent to executing the second search and prior to executing the third search, identifying the second locations based upon the first locations and the portions of the HVAC system.

16. The method of claim 12, wherein the notification is an email message.

17. A non-transitory computer-readable storage medium comprising a server electronic health records application (server EHR) that, when executed by a processor of a server computing device, causes the processor to perform acts comprising:

responsive to receiving an indication that a patient in a healthcare facility has been diagnosed with an infectious disease at a datetime, executing a first search over computer-readable tracking data stored in a computer-readable data store based upon an identifier for the patient, wherein the first search produces first search results, the first search results comprising first locations in the healthcare facility in which the patient was present within a time period that extends from the datetime to a predefined amount of time prior to the datetime;

responsive to executing the first search, executing a second search over computer-readable healthcare facility layout data stored in the computer-readable data store based upon the first locations, wherein the second search produces second search results, the second search results comprising:

portions of a heating, ventilation, and air conditioning (HVAC) system of the healthcare facility that connect the first locations in the healthcare facility to second locations in the healthcare facility; and historical operating data for the HVAC system, wherein the historical operating data for the HVAC system comprises time periods during which the portions of the HVAC system were operating such that air was flowing from the first locations to the second locations and an intensity level at which the portions of the HVAC system operated during the time periods;

subsequent to executing the second search, executing a third search over the computer-readable tracking data stored in the computer-readable data store based upon the first locations, the second locations, and the time period in which the patient was present in the first locations in the healthcare facility to identify a person that has been potentially exposed to the infectious disease, wherein the server EHR determines that the person has potentially been exposed to the infectious disease based upon the historical operating data for the HVAC system; and causing a notification to be transmitted, over a network connection, to a computing device operated by the person, wherein the notification includes an identifier for the infectious disease, an indication of the time period, and information about the infectious disease, and further wherein the notification is presented on a display of the computing device.

18. The non-transitory computer-readable storage medium of claim 17, wherein the notification is a short message service (SMS) text message.

19. The non-transitory computer-readable storage medium of claim 17, wherein the person is a second patient.

* * * * *